United States Patent
Safai et al.

(10) Patent No.: US 9,995,670 B2
(45) Date of Patent: Jun. 12, 2018

(54) METHOD OF CONTROLLING A LASER BOND INSPECTION SYSTEM

(71) Applicant: THE BOEING COMPANY, Huntington Beach, CA (US)

(72) Inventors: Morteza Safai, Newcastle, WA (US); Gary E. Georgeson, Tacoma, WA (US)

(73) Assignee: THE BOEING COMPANY, Chicago, IL (US)

( * ) Notice: Subject to any disclaimer, the term of this patent is extended or adjusted under 35 U.S.C. 154(b) by 76 days.

(21) Appl. No.: 14/963,779

(22) Filed: Dec. 9, 2015

(65) Prior Publication Data

US 2017/0167969 A1   Jun. 15, 2017

(51) Int. Cl.
*G01N 25/00* (2006.01)
*G01N 19/04* (2006.01)
*H01S 3/00* (2006.01)

(52) U.S. Cl.
CPC ............ *G01N 19/04* (2013.01); *G01N 25/00* (2013.01); *G01N 2203/0055* (2013.01); *G01N 2203/0057* (2013.01); *G01N 2203/0647* (2013.01); *G01N 2203/0694* (2013.01); *H01S 3/0014* (2013.01)

(58) Field of Classification Search
CPC .......... G01N 19/04; G01N 3/08; G01N 25/72; G01N 29/2418; G01N 2291/02881; G01N 29/228; G01N 2291/0231; G02B 6/32; G02B 6/4204; G02B 6/0288; G02B 6/34; G02B 27/0006; G02B 1/11; G01K 1/02; G01K 11/006; G01K 2213/00; G01J 2005/0077
See application file for complete search history.

(56) References Cited

U.S. PATENT DOCUMENTS

| | | | |
|---|---|---|---|
| 7,044,634 B2 * | 5/2006 | Sandvoss | G01N 25/72 374/121 |
| 8,132,460 B1 * | 3/2012 | Toller | G01N 29/2412 73/588 |
| 2004/0028113 A1 * | 2/2004 | Schlagheck | G01N 25/72 374/57 |
| 2005/0169346 A1 * | 8/2005 | Murray, Jr. | B23K 26/032 374/121 |
| 2008/0137105 A1 * | 6/2008 | Howard | G01N 25/72 356/630 |
| 2014/0049773 A1 * | 2/2014 | Lahrman | G01N 21/8422 356/237.1 |

(Continued)

OTHER PUBLICATIONS

U.S. Appl. No. 13/791,207, filed Mar. 8, 2013.
(Continued)

*Primary Examiner* — Harshad R Patel
*Assistant Examiner* — Brandi Hopkins
(74) *Attorney, Agent, or Firm* — Armstrong Teasdale LLP

(57) ABSTRACT

A method of laser bond inspection is provided. The method includes applying a thermochromatic energy-absorbing material to an inspection site of a test article. The method includes delivering a first amount of energy to the inspection site using a laser. The first amount of energy generates stresses in the test article. The method includes absorbing the first amount of energy into the thermochromatic energy-absorbing material to produce an observable thermal response that correlates to the first amount of energy.

18 Claims, 5 Drawing Sheets

(56) References Cited

U.S. PATENT DOCUMENTS

2014/0273240 A1    9/2014  Georgeson et al.
2015/0122046 A1*    5/2015  Sokol ................ G01N 29/2418
                                                  73/800
2016/0054216 A1*    2/2016  Sokol .................... G01N 19/04
                                                  73/800
2016/0282198 A1*    9/2016  Georgeson ............. G01N 21/64

OTHER PUBLICATIONS

U.S. Appl. No. 14/259,519, filed Apr. 23, 2014.
U.S. Appl. No. 14/337,622, filed Jul. 22, 2014.
U.S. Appl. No. 14/555,364, filed Nov. 26, 2014.
U.S. Appl. No. 14/591,310, filed Jan. 7, 2015.
U.S. Appl. No. 14/591,348, filed Jan. 7, 2015.
U.S. Appl. No. 14/856,550, filed Sep. 16, 2015.

* cited by examiner

METHOD OF CONTROLLING A LASER BOND INSPECTION SYSTEM

BACKGROUND

The field of the disclosure relates generally to laser inspection and, more specifically, to laser bond inspection device and a method of laser bond inspection.

In certain areas of manufacturing, two components are bonded together to form a bonded structure. Manufacturers of such bonded structures inspect the quality of the bond through various destructive and non-destructive testing. One type of non-destructive testing is laser bond inspection, where a laser is used to pass energy into an overlay to generate a calibrated compression wave that propagates through a structure. The reflection of the calibrated compression wave generates a tensile wave that stresses the bond as the tensile wave propagates back through the structure.

BRIEF DESCRIPTION

According to one aspect of the present disclosure, a method of laser bond inspection is provided. The method includes applying a thermochromatic energy-absorbing material to an inspection site of a test article. The method includes delivering a first amount of energy to the inspection site using a laser. The first amount of energy generates stresses in the test article. The method includes absorbing the first amount of energy into the thermochromatic energy-absorbing material to produce an observable thermal response that correlates to the first amount of energy.

According to another aspect of the present disclosure, a method of controlling a laser bond inspection device (LBID) is provided. The method includes setting an energy output level for a laser of the LBID to a target amount of energy. The method includes engaging the laser to deliver a first amount of energy to an inspection site on a test article. A thermochromatic energy-absorbing material is applied to the inspection site. The method includes verifying, based on an observable thermal response of the thermochromatic energy-absorbing material to the first amount of energy, the target amount of energy was delivered to the inspection site.

According to yet another aspect of the present disclosure, a laser bond inspection system is provided. The laser bond inspection system includes a laser, a thermochromatic energy-absorbing material, and a camera. The laser is configured to deliver a first amount of energy to an inspection site of a test article. The thermochromatic energy-absorbing material is applied to the inspection site and is configured to absorb the first amount of energy. The thermochromatic energy-absorbing material is configured to generate stresses within the test article. The thermochromatic energy-absorbing material is configured to exhibit an observable thermal response to the first amount of energy. The camera is configured to capture the observable thermal response.

The features, functions, and advantages that have been discussed can be achieved independently in various embodiments or may be combined in yet other embodiments further details of which can be seen with reference to the following description and drawings.

DETAILED DESCRIPTION

As used herein, an element or step recited in the singular and proceeded with the word "a" or "an" should be understood as not excluding plural elements or steps unless such exclusion is explicitly recited. Furthermore, references to "one embodiment" of the present invention or the "exemplary embodiment" are not intended to be interpreted as excluding the existence of additional embodiments that also incorporate the recited features.

During manufacturing, two components are joined with a bond having an intended level of strength. During laser bond inspection, a calibrated amount of energy is used to generate stress in the bond. A good bond is unaffected by the stress, while a bad bond fails. Failure of a bond may be visually detectable or, in certain applications, by ultrasonic testing.

An important aspect of laser bond inspection is the ability to deliver a calibrated amount of energy to an energy absorbing overlay using the laser. Too little energy may not adequately test the bond, and too much energy may destroy a good bond. It is realized herein applying a thermochromatic material to an energy absorbing overlay at a laser bond inspection site on a test article provides immediate indication of energy transfer into the energy absorbing overlay and the test article. The thermochromatic material exhibits a thermal response to the energy transfer from the laser by changing color and intensity. The thermal response is observable under a selected wavelength of light, such as, for example, ultraviolet (UV) light. For example, the thermal response may be captured using a charge coupled device (CCD) or CMOS type camera under UV light. In certain embodiments, the thermal response is observable visually by a user of the laser bond inspection system in the normal human-visible spectrum. The thermal response produces a spectrum of colors corresponding to a range of energy absorbed. For a particular bond to be tested using a particular amount of energy, the appropriate amount of energy transfer from the laser to the energy absorbing overlay is verified by comparing the resulting color change of the thermochromatic material with an expected color in the spectrum. Similarly, too little or too much energy transfer produces distinct colors in the spectrum.

Figure 1:
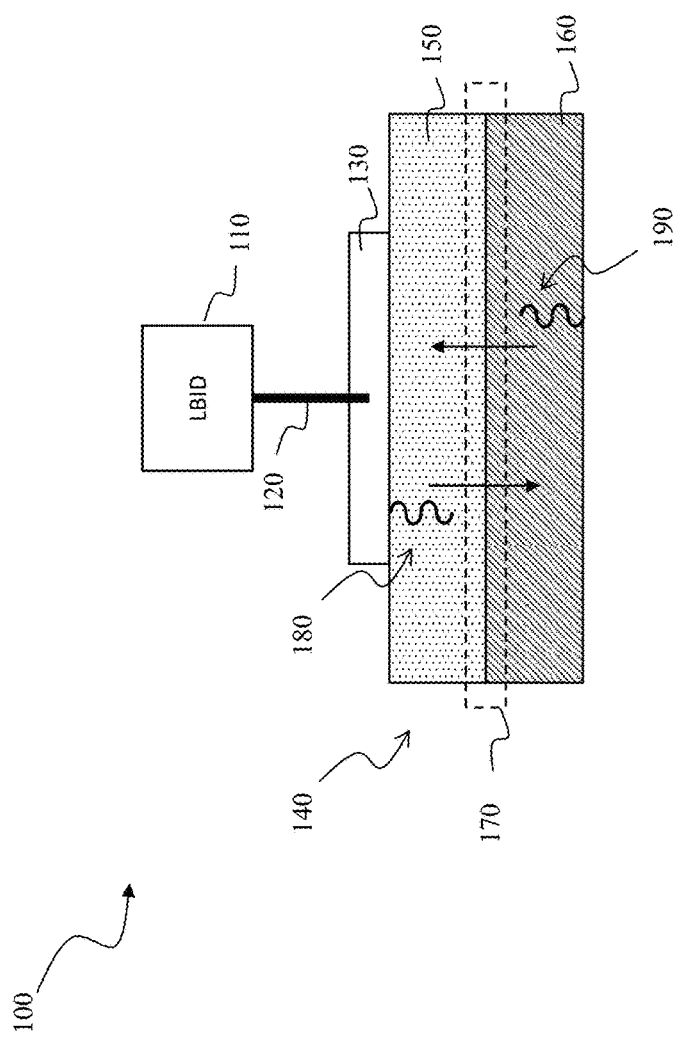
FIG. 1 is diagram of one embodiment of a laser bond inspection system.

FIG. 1 is block diagram of a laser bond inspection system 100. Laser bond inspection system 100 includes a laser bond inspection device 110 configured to generate a laser beam 120. Laser bond inspection system 100 also includes a thermochromatic energy-absorbing material 130 applied to an inspection site of a test article 140. Test article 140 includes a first component 150 and a second component 160 joined by a bond 170. Thermochromatic energy-absorbing material 130 may include a homogeneously thermochromatic material. In alternative embodiments, thermochromatic energy-absorbing material 130 may include an energy-absorbing material coated with a thermochromatic material, such that the coating layer is thermochromatic, but the energy-absorbing material is not.

During operation, LBID 110 generates and directs laser beam 120 toward test article 140. Laser beam 120 is configured to deliver a calibrated amount of energy to the inspection site. The calibrated amount of energy varies for each test article. For test article 140, a target amount of energy is computed that will produce a target amount of stress in test article 140 to test bond 170. The amount of energy actually delivered by laser beam 120 may vary during operation of LBID 110.

The energy delivered by laser beam 120 is absorbed by thermochromatic energy-absorbing material 130. The absorbed energy creates a compression wave 180 that propagates through test article 140. When compression wave 180 reaches the rear face of test article 140, it is reflected back toward thermochromatic energy-absorbing material 130 as a tensile wave 190. Tensile wave 190 stresses bond 170. The target amount of energy is determined such that tensile wave 190 delivers the target amount of stress in test article 140. If too little energy is absorbed, from laser beam 120, into thermochromatic energy-absorbing material 130, the amount of stress generated by tensile wave 190 will not be sufficient to properly test bond 170. If too much energy is absorbed into thermochromatic energy-absorbing material 130, from laser beam 120, the amount of stress generated by tensile wave 190 may exceed the strength of a good bond, thus damaging an otherwise good bond.

Thermochromatic energy-absorbing material 130 is configured to exhibit an observable thermal response to the energy delivered by laser beam 120 and absorbed into thermochromatic energy-absorbing material 130. The observable thermal response includes, for example, color change and intensity change. The target amount of energy for test article 140 causes an expected thermal response in thermochromatic energy-absorbing material 130 that correlates to the target amount of energy. The expected thermal response may include, for example, a specific color and intensity. If laser beam 120 delivers too little energy to thermochromatic energy-absorbing material 130, a distinct thermal response is exhibited, the distinct thermal response correlating to the actual amount of energy absorbed. If laser beam 120 delivers too much energy to thermochromatic energy-absorbing material 130, another distinct thermal response is exhibited and correlates to the actual amount of energy absorbed.

Figure 2:
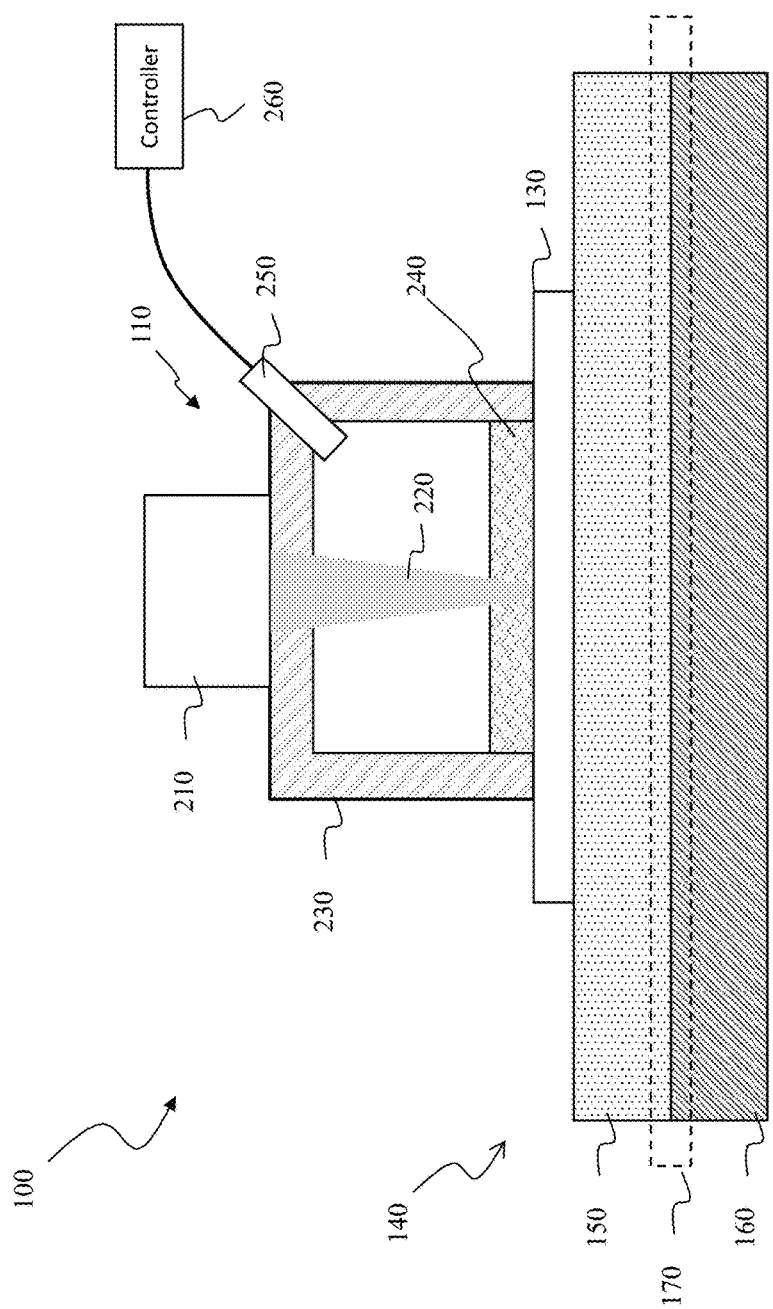
FIG. 2 is a cross-sectional diagram of the laser bond inspection system shown in FIG. 1.

FIG. 2 is a cross-sectional diagram of the laser bond inspection system 100 shown in FIG. 1. LBID 110 includes a laser source 210 configured to generate a laser beam 220. LBID 110 includes a vacuum chamber 230 that, when joined with thermochromatic energy-absorbing material 130, is configured to generate a vacuum within which laser beam 220 propagates. A layer of water 240 is disposed within vacuum chamber 230 at thermochromatic energy-absorbing material 130 to contain pressure buildup at the inspection site of test article 140.

LBID 110 further includes a camera 250 configured to capture the observable thermal response exhibited by thermochromatic energy-absorbing material 130 during operation. In certain embodiments, camera 250 includes a charge coupled device. In alternative embodiments, camera 250 may include an infrared camera or an optical camera. In certain embodiments, LBID 110 includes an ultraviolet (UV) light source for illuminating the inspection site while camera 250 captures the observable thermal response.

In certain embodiments, laser bond inspection system 100 includes a controller 260 configured to receive images from camera 250. Controller 260 is further configured to process an image of the observable thermal response to determine a difference between the energy absorbed into thermochromatic energy-absorbing material 130 and the target amount of energy. In certain embodiments, controller 260 is configured to compute a chromatic value for the energy absorbed that is compared to a predetermined chromatic value for the target amount of energy. Controller 260 is configured to adjust laser source 210 to deliver a second amount of energy to compensate for the determined difference between the target amount of energy and the first amount of energy actually delivered. For example, controller 260 increases the energy level of laser beam 220 if the first amount of energy delivered is less than the target amount of energy. Conversely, controller 260 decreases the energy level of laser beam 220 if the first amount of energy delivered is greater than the target amount of energy.

Figure 3:
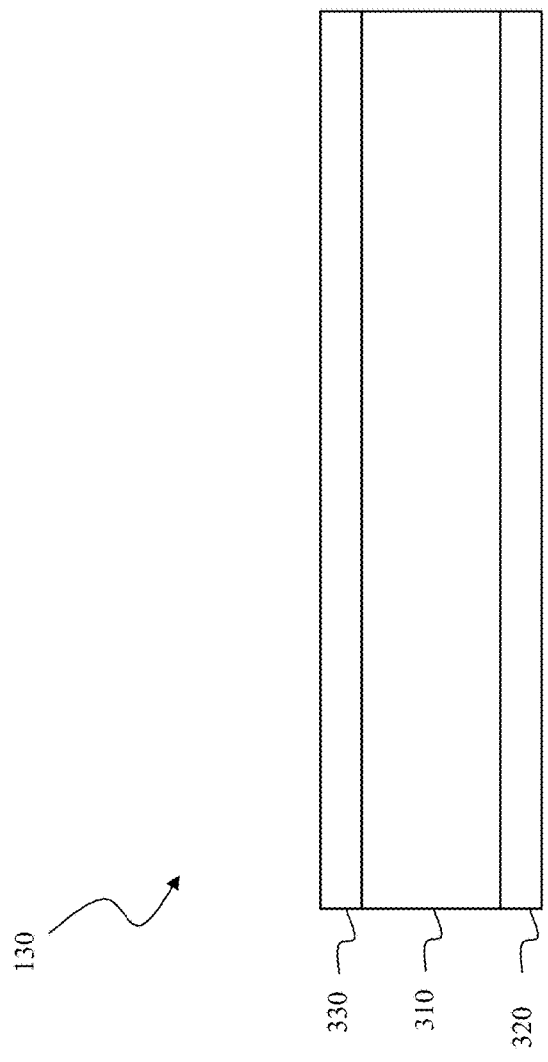
FIG. 3 is a cross-sectional diagram of one embodiment of a thermochromatic energy-absorbing material.

FIG. 3 is a cross-sectional diagram of thermochromatic energy-absorbing material 130 shown in FIGS. 1 and 2. Thermochromatic energy-absorbing material 130 includes an energy absorbing overlay 310. Energy absorbing overlay 310 includes a first surface having an adhesive layer 320 that facilitates adhesively coupling energy absorbing overlay 310 to a test article, such as test article 140 shown in FIGS. 1 and 2. Energy absorbing overlay 310 includes a second surface opposite the first surface. The second surface has a thermochromatic material 330 applied such that energy absorbed into energy absorbing overlay 310 generates an observable thermal response in thermochromatic material 330.

In certain embodiments, for example, energy absorbing overlay 310 is manufactured as a roll of tape that can be applied along bond lines in various test articles.

In alternative embodiments, energy absorbing overlay 310 has thermochromatic properties such that energy-absorbing material 130 is homogeneously thermochromatic, with the exception of adhesive layer 320. In such a material, thermochromatic material 330 is omitted, as energy absorbing overlay 310 has the desired thermochromatic properties.

Figure 4:
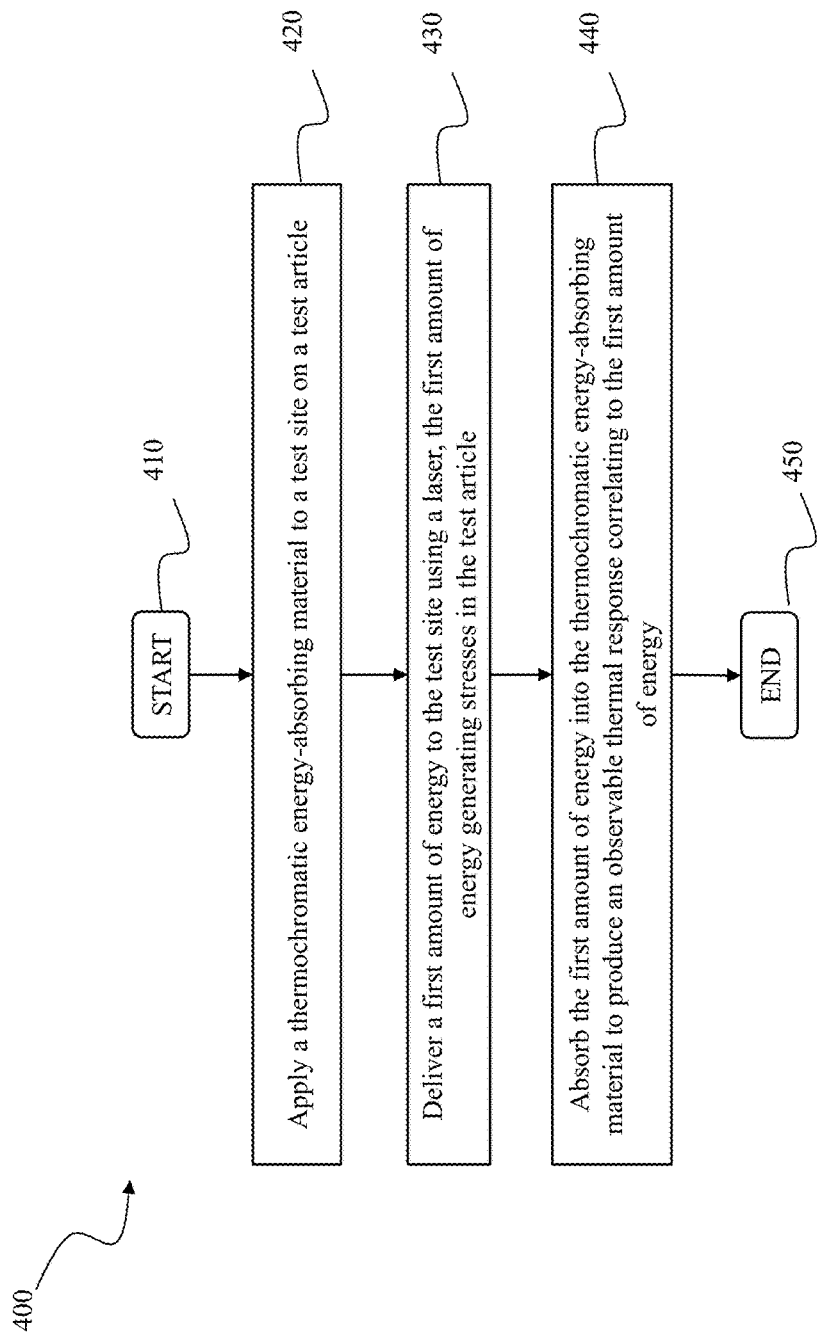
FIG. 4 is a flow diagram of one embodiment of a method of laser bond inspection.

FIG. 4 is a flow diagram of one embodiment of a method 400 of laser bond inspection of a test article. Method 400 includes a start step 410. At a preparation step 420, a thermochromatic energy-absorbing material is applied to an inspection site of the test article. In certain embodiments, applying the thermochromatic energy-absorbing material includes applying a thermochromatic energy-absorbing tape over a bond line of the test article.

At a delivery step 430, a first amount of energy is delivered to the inspection site using a laser. The first amount of energy generates stresses in the test article. In certain embodiments, method 400 includes a computing step where a target amount of energy to be delivered is computed based on a target amount of stress to be applied to the test article.

At an absorbing step 440, the first amount of energy is absorbed into the thermochromatic energy-absorbing material to produce an observable thermal response that correlates to the first amount of energy. The observable thermal response facilitates immediate feedback of the amount of energy delivered by the laser.

In certain embodiments, method 400 includes a capture step during which the observable thermal response is captured and analyzed. Based on a captured observable thermal response, the laser bond inspection system determines whether the first amount of energy is less than or greater than the target amount of energy. The captured observable thermal response is compared to an expected thermal response correlating to the target amount of energy. In certain embodiments, the observable thermal response is quantifiable as a chromatic value correlating to the first amount of energy absorbed. If, for example, the first amount of energy delivered is less than the target amount of energy, a second amount of energy is computed that is greater than the first amount of energy. The second amount of energy is then delivered to a second inspection site. The process can be repeated as necessary until the test article is sufficiently tested.

In certain embodiments, capturing the observable thermal response is carried out using a camera. In certain embodiments, the inspection site is illuminated by a UV light source to facilitate capture of the observable thermal response. An image of the observable thermal response captured by the camera is then processed. In certain embodiments, the image is processed to determine a chromatic value for the observable thermal response that is compared to a chromatic value for the target amount of energy.

In certain embodiments, a user observes the thermal response or the image of the thermal response to determine whether the target amount of energy was delivered.

In certain embodiments, method 400 includes a calibration step before preparation step 420. During the calibration step, the thermochromatic energy-absorbing material is applied to a calibration article. The laser is then used to deliver the target amount of energy to the thermochromatic energy-absorbing material on the calibration article to verify the laser is delivering the appropriate amount of energy and producing the expected thermal response in the thermochromatic energy-absorbing material prior to inspecting the test article. In certain embodiments, the calibration step is repeated periodically to re-verify the energy output of the laser.

The method ends at an end step 450.

Figure 5:
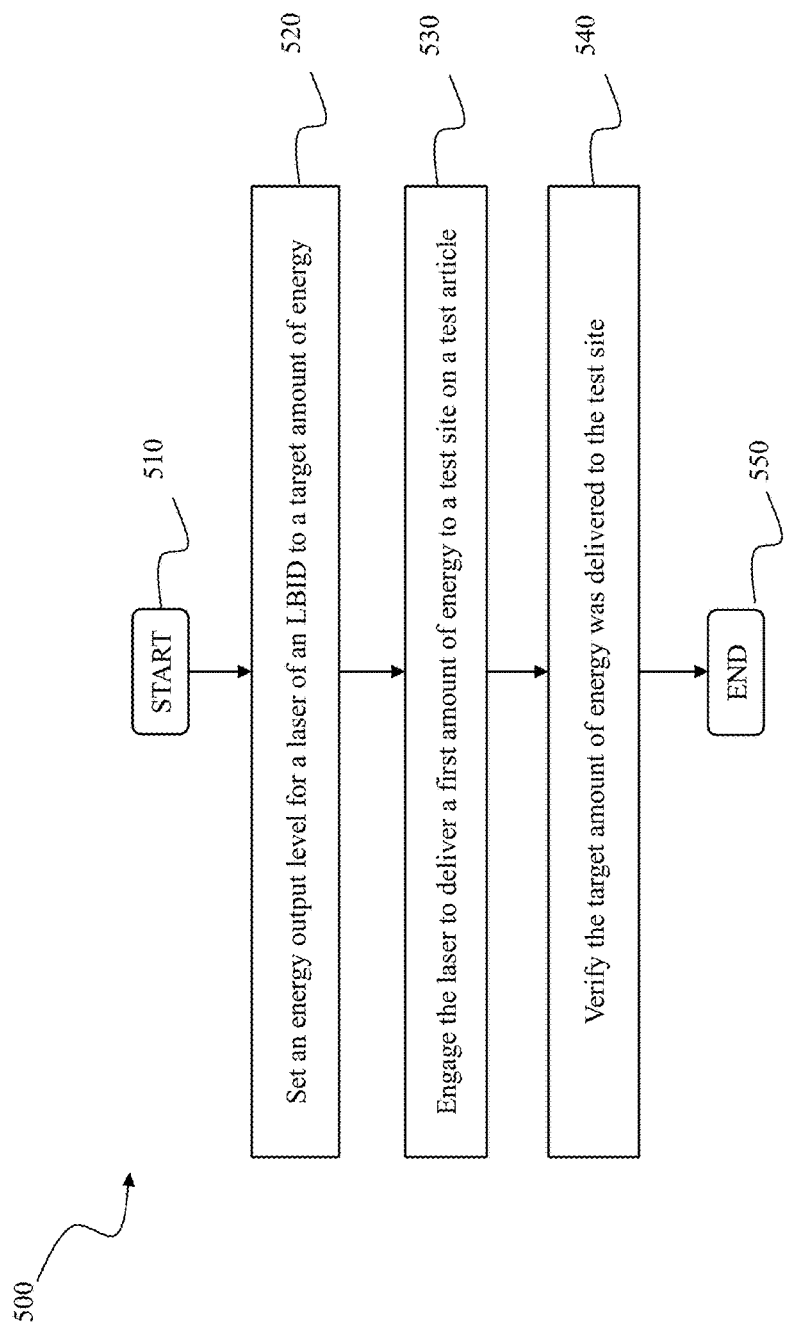
FIG. 5 is a flow diagram of one embodiment of a method of controlling a laser bond inspection device.

FIG. 5 is a flow diagram of one embodiment of a method 500 of controlling a laser bond inspection device (LBID). The method begins at a start step 510. At a setup step 520, an energy output level for a laser of the LBID is set to a target amount of energy. At a delivery step 530, the laser is engaged to deliver a first amount of energy to an inspection site of a test article. The test article has a thermochromatic energy-absorbing material applied at the inspection site. The thermochromatic energy-absorbing material is configured to absorb the first amount of energy delivered by the laser. The thermochromatic energy-absorbing material is further configured to exhibit an observable thermal response to the first amount of energy absorbed.

At a verification step 540, the LBID verifies the target amount of energy was delivered to the inspection site based on the observable thermal response exhibited by the thermochromatic energy-absorbing material to the first amount of energy. If the first amount of energy is equal to or within a range of the target amount of energy, the observable thermal response will match an expected thermal response for the target amount of energy. If the observable thermal response indicates less than the target amount of energy was delivered to the inspection site, the energy output level for the laser is increased. If the observable thermal response indicates greater than the target amount of energy was delivered to the inspection site, the energy output level for the laser is decreased.

In certain embodiments, the observable thermal response is measured, or quantified for comparison to the expected thermal response. Such a measurement may be made manually by a user, or may be captured and computed using a camera, spectrophotometer, or other instrument. In certain embodiments, method 500 includes a feedback step where the observed thermal response is used to adjust a fluence of the laser.

In certain embodiments, verification step 540 includes capturing the observable thermal response of the thermochromatic energy-absorbing material to the first amount of energy. Once captured, the observable thermal response is compared to the expected thermal response for the target amount of energy. In certain embodiments, comparing the observable thermal response to the expected thermal response includes computing a first chromatic value for the observable thermal response and comparing the first chromatic value to a second chromatic value for the expected thermal response and correlating to the target amount of energy.

The method ends at an end step 550.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of controlling a laser bond inspection device (LBID) having a laser and a camera, the method comprising:
   setting an energy output level for the laser of the LBID to a target amount of energy;
   engaging the laser to deliver a first amount of energy to an inspection site on a test article, the inspection site having a thermochromatic energy-absorbing material applied thereto;
   observing, using the camera, an observable thermal response of the thermochromatic energy-absorbing material to the first amount of energy; and
   verifying, based on the observable thermal response, the target amount of energy was delivered to the inspection site.

2. The method of claim 1 further comprising increasing the energy output level for the laser if the observable thermal response indicates less than the target amount of energy was delivered to the inspection site.

3. The method of claim 1 further comprising decreasing the energy output level for the laser if the observable thermal response indicates more than the target amount of energy was delivered to the inspection site.

4. The method of claim 1, wherein verifying the target amount of energy was delivered to the inspection site comprises:
   capturing the observable thermal response of the thermochromatic energy-absorbing material to the first amount of energy; and
   comparing the observable thermal response to an expected thermal response correlating to the target amount of energy.

5. The method of claim 4, wherein comparing the observable thermal response to the expected thermal response comprises:
   computing a first chromatic value of the observable thermal response; and
   comparing the first chromatic value to a second chromatic value correlating to the target amount of energy.

6. The method of claim 1 further comprising computing the target amount of energy to be delivered based on a target amount of stress to be applied to the inspection site.

7. The method of claim 6, wherein observing comprises capturing the observable thermal response and verifying comprises determining the first amount of energy is less than the target amount of energy based on comparing the observable thermal response to an expected thermal response correlating to the target amount of energy.

8. The method of claim 7 further comprising:
computing a second amount of energy to be delivered, wherein the second amount of energy is greater than the first amount of energy; and
delivering the second amount of energy to a second inspection site using the laser.

9. The method of claim 6, wherein capturing the observable thermal response comprises capturing the observable thermal response using the camera.

10. The method of claim 1, wherein observing the observable thermal response comprises capturing the observable thermal response using the camera.

11. The method of claim 10, wherein capturing the observable thermal response further comprises illuminating the inspection site using an ultraviolet (UV) light source for capture by the camera.

12. The method of claim 10 further comprising computing a chromatic value correlating to the first amount of energy based on the observable thermal response captured in an image by the camera.

13. The method of claim 10, wherein using the camera comprises using a charge coupled device.

14. The method of claim 10 further comprising receiving an image of the observable thermal response captured by the camera at a controller.

15. The method of claim 14 further comprising processing the image, at the controller, to determine a difference between the first amount of energy absorbed into the thermochromatic energy-absorbing material and the target amount of energy.

16. The method of claim 15 further comprising computing, at the controller, a second amount of energy to compensate for the difference.

17. The method of claim 16 further comprising adjusting the laser to deliver the second amount of energy.

18. The method of claim 1 further comprising generating a vacuum within a vacuum chamber within which the first amount of energy is to be delivered to and absorbed by the thermochromatic energy-absorbing material.

* * * * *